United States Patent [19]

Guyton

[11] Patent Number: 4,552,440
[45] Date of Patent: Nov. 12, 1985

[54] APPARATUS FOR DETERMINATION OF POTENTIAL VISUAL ACUITY UTILIZING A SLIT LAMP MICROSCOPE

[76] Inventor: David L. Guyton, 307 Somerset Rd., Baltimore, Md. 21210

[21] Appl. No.: 541,305

[22] Filed: Oct. 12, 1983

[51] Int. Cl.[4] .............................................. A61B 3/10
[52] U.S. Cl. ..................................... 351/214; 351/211
[58] Field of Search ............... 351/211, 205, 217, 218, 351/214

[56] References Cited

U.S. PATENT DOCUMENTS

| | | | |
|---|---|---|---|
| 1,755,705 | 4/1930 | Reid | 351/211 |
| 4,196,980 | 4/1980 | Heine | 351/211 |
| 4,220,401 | 9/1980 | Muchel | 351/211 |
| 4,272,165 | 6/1981 | Muchel | 351/211 |

Primary Examiner—Rodney B. Bovernick
Attorney, Agent, or Firm—Dennison, Meserole, Pollack & Scheiner

[57] ABSTRACT

In order to determine the visual acuity in the human eye in the presence of cataracts or other opacities, a conventional slit lamp microscope having an illumination source, an aperture illuminated thereby, and a converging lens, has been modified by the insertion of a target transparency having test figures thereon between the aperture and converging lens. The inclusion of a set of trial lenses positioned adjacent to the eye to neutralize refractive error, movement axially of the target transparency, and the inclusion of a telescopic optical system also axially adjustable is contemplated.

11 Claims, 7 Drawing Figures

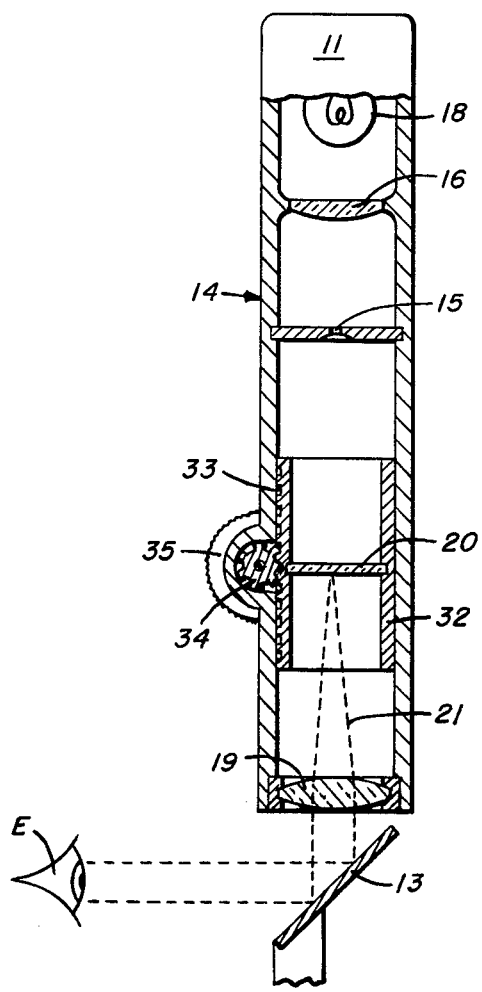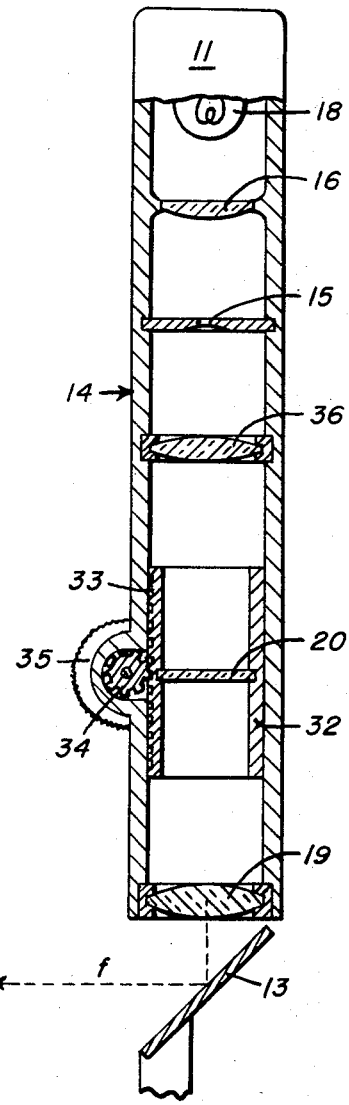

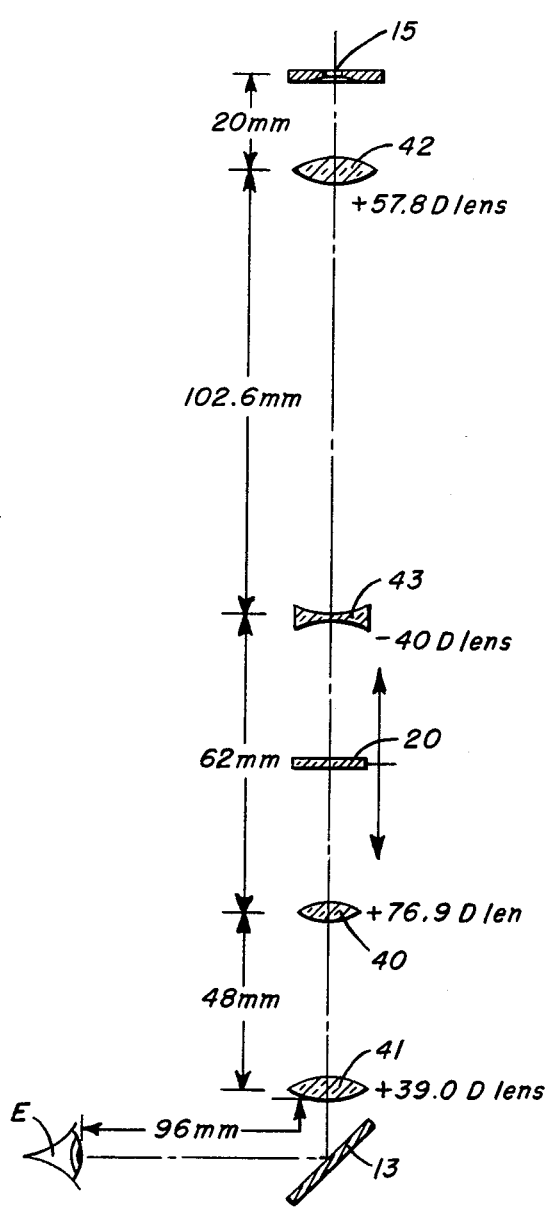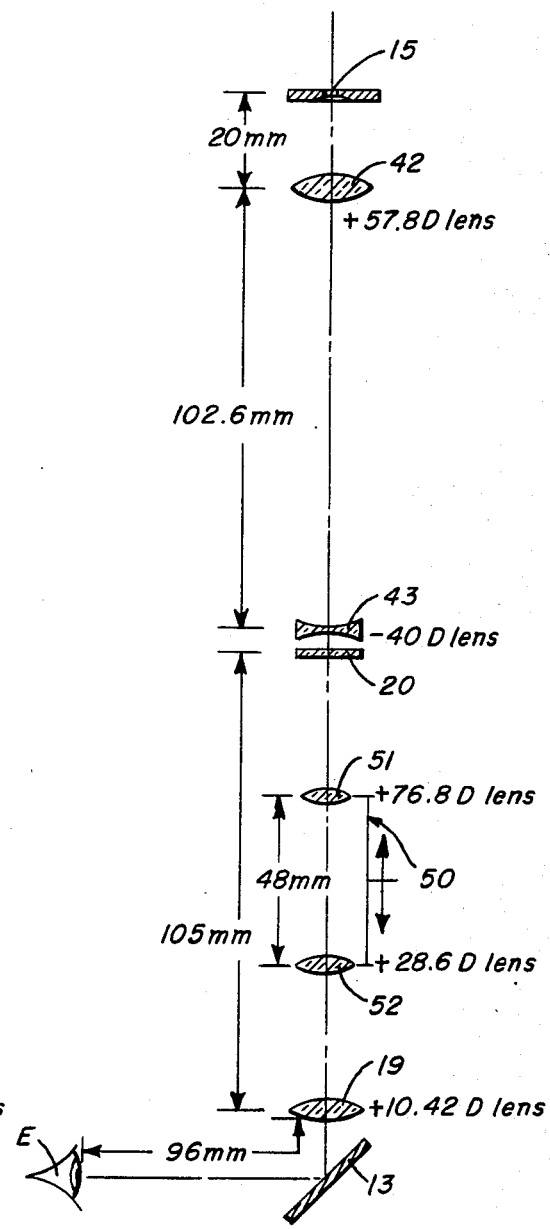

APPARATUS FOR DETERMINATION OF POTENTIAL VISUAL ACUITY UTILIZING A SLIT LAMP MICROSCOPE

BACKGROUND OF THE INVENTION

The present invention relates broadly to the field of vision testing and more particularly to apparatus for determination of potential retinal acuity in the human eye in the presence of opacities as frequently caused by cataracts and the like.

It is clinically important for the ophthalmologist to determine the potential visual acuity of the retina in comparison to the existing or actual visual acuity in patients with corneal disease, cataracts, or other diseases of the eye causing opacities or irregularity of the optical media. The determination as to whether or not surgery is indicated in such situations will depend largely on the improvement in the visual acuity that might reasonably be expected with such surgery. It is not infrequent for a patient to have 20/200 vision coexisting with a cataract and macular changes such as drusen or pigment epithelial changes. Frequently, the cataract that exists does not, to the ophthalmologist, appear dense enough to account for the visual loss and therefore there is always concern about significant posterior disease. For these reasons, the determination of the potential retinal acuity of the patient in the presence of the media opacities is quite important to the ocular surgeon.

DISCUSSION OF THE PRIOR ART

Various methods have been used in the past to nullify refractive error as well as to bypass the opacities in the eye's optical media for the purpose of forming images on the retina to determine the visual acuity. Of all of these methods in the prior art, the pinhole aperture and the use of interference fringes have been most popular. Additional techniques that are used to test retinal function include a sense of light projection, echography, electroretinography, color vision, pupil function, entoptic phenomena, Haidinger's brushes phenomenon, and the use of the visually evoked response. It has been found that these techniques only provide very gross estimates of macular function.

The pinhole aperture has been used for over a century to nullify small amounts of refractive error during visual acuity testing. By placing an aperture of about 1 millimeter in diameter before the pupil there is an increase in the depth of focus of the eye to an extent that good visual acuity can frequently be obtained even in the presence of a refractive error of the order of 2 to 3 diopters. Unfortunately, the depth of focus of the eye cannot be increased further by this method. It is found that if the diameter of the pinhole is smaller than about 1 millimeter, diffraction at the edges of the aperture will interfere with the image obtained so that visual acuity does not increase further and in fact will often decrease.

In addition to its use in nullifying small refractive errors, the pinhole aperture is often used to bypass corneal scars or other irregularities which cause decreased visual acuity by scattering the light entering the eye. The pinhole aperture is used to isolate a portion of the eye's optics which is relatively free from such irregularities or scar, thus allowing determination of retinal visual acuity in the absence of scattered light. (*American Journal of Ophthalmology* 33: 1612-1614, 1950). Because of the relatively small size of clear areas in diseased corneas or cataracts, on the order of a fraction of a millimeter, it is frequently impossible with a 1 millimeter pinhole aperture to isolate a suitable window without surrounding scatter. While better isolation could be obtained with a smaller pinhole, the diffraction problem noted above with decrease of visual acuity prevents the use of such smaller apertures. Accordingly, the pinhole aperture is limited by the phenomenon of diffraction, and this limitation affects both its ability to nullify refractive error and its ability to isolate small windows in the eye's optics. The result is the doubt that remains in the mind of the physician as to whether the best potential visual acuity has in fact been obtained.

The other popular method for determining best potential retinal visual acuity is the use of interference fringes of variable frequency. Green and Cohen in an article entitled "Laser Interferemetry In The Evaluation Of Potential Macular Function In The Presence Of Opacities In The Ocular Media", published in *Trans. Amer. Acad. Ophth. Otol.* 75: 629-637 (May-June, 1971) discuss this technique. Such interference fringes have generally been produced by forming a double image of a coherent light source, usually a laser, in the vicinity of the pupil of the eye so that two overlapping bundles of coherent light are caused on the retina. Interference fringes are produced within the overlap region, with frequency dependent on the separation of the double images within the pupil. This method is effective in nullifying refractive error of the eye, for the contrast of the interference fringes is independent of the refractive error, and although the fringe frequency may be influenced by uncorrected refractive error and eyeball length, the effects are small.

In use, the patient is asked to indicate to the examiner the direction of the interference fringes, as the direction is changed by the examiner, to determine whether he can resolve the fringes. The fringe frequency is gradually increased, corresponding to better visual acuity, until the limit of resolution is reached.

Since only pinpoint areas of the eye's optics are essential for passage of the two coherent beams of light, it is usually possible either by trial-and-error or by aiming the beams under microscopic observation (see Rassow, U.S. Pat. No. 4,125,320), to locate areas between ocular opacities that will allow adequate passage. Therefore, this system not only nullifies refractive error but also bypasses opacities or irregularities in the eye. On the other hand, the interference fringe method has some limitations as noted by Green and Cohen, supra. Many patients are unaccustomed to such looking for fringe patterns and will have difficulty appreciating high frequency patterns. Further, changing fringe frequency is a time-consuming act on the part of the examiner, and the examiner/patient interaction in determining the direction of the fringes for each spacing becomes quite tedious. Interference fringe acuity may not correlate with letter acuity obtained by conventinal measurement systems. The major limitation with the fringe method is the necessity to locate two precisely spaced clear areas in the eye's optics for the simultaneous passage of the coherent beams. An opacity can conceivably block one beam entirely, and translucency can destroy the coherence of the light. It is frequently difficult if not impossible to locate two clear areas, even under slit lamp microscopic control.

A further method for determining best potential retinal visual acuity was described by Cavonius and Hilz in an article entitled "A Technique for Testing Visual Function in the Presence of Opacities," published in *Investigative Ophthalmology* 12:933-936 (December, 1973). A small light source is imaged by a converging lens into the patient's pupil (a "Maxwellian view" arrangement). A target transparency containing figures or letters for determination of visual acuity is placed in the optical pathway between the light source and the converging lens. The visual acuity figures are thus viewed by the patient in silhouette and may be brought into focus by adjustment of the target transparency along the optical axis. Such axial adjustment of the target transparency provides effective correction of the patient's refractive error according to the well-known optometer principle.

In the Cavonius and Hilz apparatus, the image of the light source in the patient's pupil behaves as a tiny aerial pinhole aperture through which the patient views the visual acuity target. Because this aerial pinhole aperture has no physical edges, there is no diffraction of light from the edges, and the size of the aerial aperture may be made much smaller than 1.0 mm without degradation from diffraction. Because of this small size, a greater depth of focus is achieved than with the conventional 1.0 mm pinhole aperture, and a smaller "window" can be isolated through the eye's optics. Only one such window need be found, a distinct advantage over the laser interference fringe method where two windows must be located simultaneously.

An instrument using the Cavonius and Hilz method was described by Minkowski, Palese, and Guyton in an article entitled "Potential Acuity Meter Using a Minute Aerial Pin-hole Aperture," published in *OPHTHALMOLOGY* 90: (in press) (1983). An illuminated aperture serves as the effective light source, and the self-contained instrument mounts on a standard slit lamp microscope with the aerial aperture of the Potential Acuity Meter fixed in the viewing plane of the microscope. The aerial pinhole aperture is only 0.1 mm in diameter. The light forming the aerial aperture is visible through the microscope, and the examiner uses the slit lamp's mechanical controls to direct the light beam through a clear area of the eye's optics. Spherical refractive correction from −10 D to +13 D is provided by axial adjustment of the visual acuity target.

Despite the advantages of the Minkowski et al potential acuity meter over the other methods of potential visual acuity testing, the device is somewhat cumbersome since a storage location must be provided and the instrument must be mounted on and unmounted from the slit lamp microscope with each use. Optical and mechanical construction must be accurate and sound to ensure proper calibration of the visual acuity figures and to ensure proper alignment of the aerial pinhole aperture with the viewing plane of the slit lamp microscope. Such construction is costly.

Accordingly, it is an object of the present invention to incorporate potential acuity testing apparatus within the illumination system of a conventional slit lamp microscope, allowing increased convenience of use and substantially reduced cost of manufacture.

A further object of the invention is to correct the refractive error of the patient's eye during potential acuity testing.

An additional object is to adjust the refractive error correction linearly in diopters.

Still a further object of the invention is to maintain constant magnification during correction of refractive error such that the calibration of the visual acuity target remains correct.

Another object of the invention is to provide an optical apparatus which is reltively simple to use and which provides complete safety to the patient during such use.

Other objects and advantages of the invention will become apparent from the following description.

SUMMARY OF THE INVENTION

The illumination system of a slit lamp microscope typically comprises an illuminated aperture and a converging lens which forms an image of the illuminated aperture in the viewing plane of the microscope for focal examination of the patient's eye of the examiner. With most slit lamp microscopes, various shapes and sizes of the illuminated apertures may be selected by means of a dial, including a small pinhole aperture. By introducing a visual acuity target transparency into the proper location between the illuminated aperture and the converging lens, potential acuity apparatus is created.

One embodiment of the invention comprises the addition of a target transparency to the slit lamp illumination system. With this embodiment, refractive error of the patient's eye must be corrected by the wearing of glasses or a contact lens during testing. Other embodiments of the invention use additional apparatus for correction of the eye's refractive error. In one such embodiment a wheel of corrective trial lenses is positioned before the patient's eye. In another embodiment, the target transparency is movable along the optical axis of the slit lamp illumination system. In still another embodiment, a telescopic lens system is movable along the optical axis to provide refractive correction. In either the movable target transparency embodiment or the movable telescopic lens system embodiment, proper choice of lens powers and spacings ensures amounts of refractive correction proportional to the axial displacement of the movable element, and also ensures constant magnification of the image of the target transparency, according to the optometer principle.

Details of the invention will become more readily apparent from the following description when taken in conjunction with the accompanying drawings.

IN THE DRAWINGS

FIG. 4 is a partial cross-sectional view of the illumination system of a slit lamp microscope, containing a target transparency movable along the optical axis, and representing a modified form of the invention.

FIG. 5 is a partial cross-sectional view of the illumination system of a slit lamp microscope, representing an adaption of the apparatus of FIG. 4, wherein the posterior focal plane of the converging lens is proximate to the patient's eye.

FIG. 6 is a schematic illustration of an adaptation of the apparatus of FIG. 5, wherein a wide range of refractive error correction is provided.

FIG. 7 is a schematic illustration of an adaptation of FIG. 1, including the addition of a collimating lens system and a movable telescopic lens system.

DESCRIPTION OF THE PREFERRED EMBODIMENTS

Figure 1:
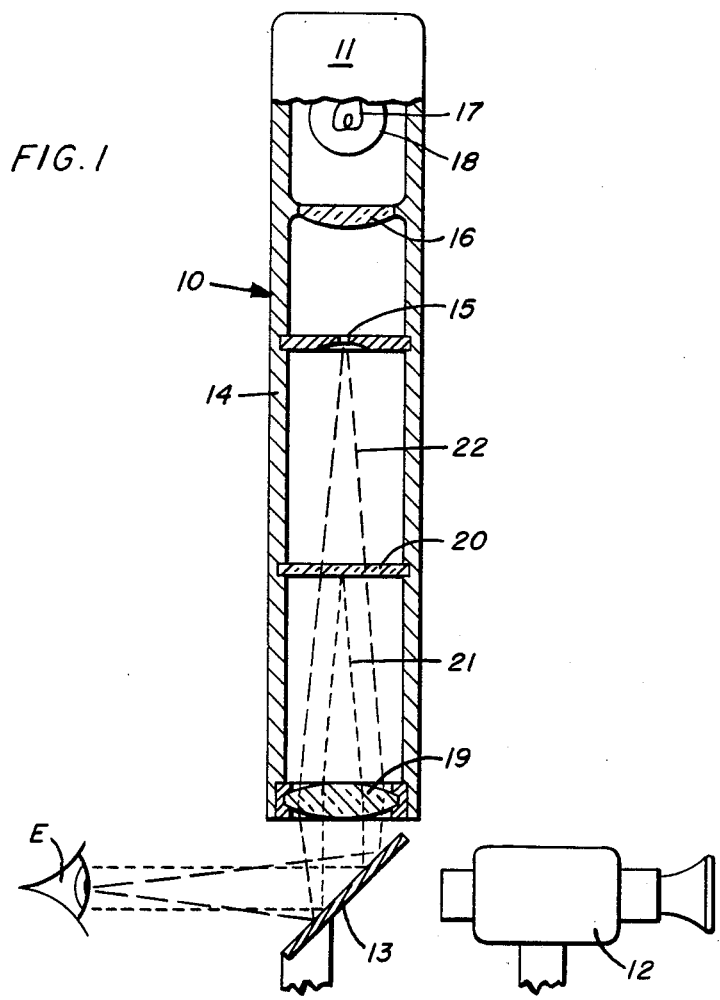
FIG. 1 is a partial cross-sectional view of a slit lamp microscope showing the added target transparency of the invention in fixed position.

Referring to the aparatus of FIG. 1, a typical slit lamp microscope 10 has two basic components, the illumination system 11 and the microscope 12. The microscope is a binocular stereo microscope with the two viewing axes capable of passing to either side of the 45 degree mirror 13 of the illumination system. The illumination system includes a tubular casing preferably of metal 14 in which the various components are mounted. A wheel of selectable apertures is typically provided, but for simplicity only the pinhole aperture 15 is shown in the figure. A condensing lens 16 focuses the filament 17 of the lamp 18 onto the surface of the converging lens 19 which is mounted at the lower end of the illumination system housing 14, rather than focusing it at the aperture position 15. The light illuminates the aperture, however, and the aperture thus becomes the effective light source for eventual focal illumination of the patient's eye. The converging lens 19 forms an image of the illuminated aperture at the patient's eye, shown at E, such that the examiner, in viewing through the microscope, can examine small areas of the patient's eye under focal illumination. Ordinarily a slit aperture is used for examination, hence the name slit lamp microscope, but round apertures of various sizes are also provided, including a small pinhole aperture, typically 0.2 mm in diameter.

The target transparency 20 is fixed in position in housing 14 between the illuminated aperture 15 and the converging lens 19, such that the figures on the target transparency are seen in silhouette by the patient. It is convenient to place the target transparency in the vicinity of the anterior focal plane of the converging lens as shown in FIG. 1, whereby the image of the target transparency viewed by the patient is located in the distance. If the target transparency 20 is placed exactly in the anterior focal plane of the converging lens, the image of the target transparency viewed by the patient will appear at optical infinity, the correct position for viewing by an eye with no refractive error. Dotted rays of light from an object point on the target transparency are shown at 21 in FIG. 1 as being made parallel by the converging lens 19, indicating that the image of that object point is formed at infinity. Dashed rays of light 22 from the illuminated aperture on the other hand, are shown as being brought to focus at the eye E by the converging lens 19, forming an aerial pinhole aperture, through which all light emerging from the illumination system must pass. The dotted rays of light 21, therefore, only show the focusing characteristics of the converging lens, for these rays of light do not actually exist. It may be appreciated that if the illuminated aperture is small enough, only a single light ray passes through each point of the target transparency 20, with all of the single light rays being gathered by the converging lens 19 and made to pass through the aerial pinhole aperture at the eye.

Figure 2:
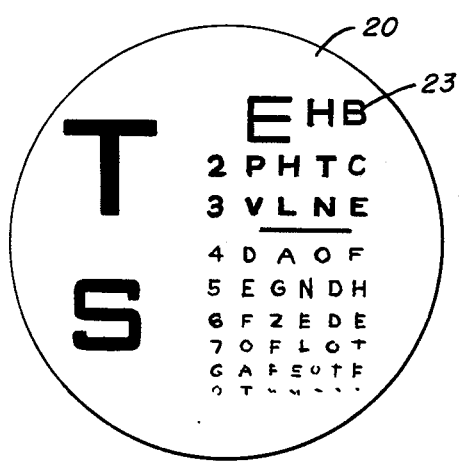
FIG. 2 is a plan view of the target transparency of FIG. 1.

With the target transparency in FIG. 1 in a fixed position as shown, the visual acuity figures on the target transparency can be of a fixed calibrated size for determining various levels of visual acuity. For example, the image of the 20/20 letters which is presented to the eye by the converging lens 19 must subtend 5 minutes of arc in height. 20/200 letters must subtend 50 minutes of arc in height, and so forth. As can be seen from FIG. 2, the target transparency 20 contains a typical visual acuity chart having visual acuity figures 23 of various calibrated sizes.

It should be appreciated that the present invention is not limited to a target transparency which is permanently mounted in place within the body of the illumination system of the slit lamp microscope. The target transparency can be mounted in such a way as to be introducable only when needed, or several target transparencies, each having a different visual acuity chart, could be mounted for introduction by manual selection if desired. It should be further noted, however, that the permanent presence of a target transparency within the illumination system does not seriously affect the performance of the illumination system for ordinary slit lamp microscope operation, for the total area covered by the opaque letters against the transparent background is quite minimal. The advantage of having the target transparency permanently in place is the ease of operation. All that is necessary to activate the potential visual acuity measurement is the manual dialing in of the proper illuminated aperture. The advantage of having selectable target transparencies, on the other hand, is that different visual acuity charts may be used, having smaller and larger visual acuity figures, and also having alternate figures of the same size for patients who tend to memorize the figures.

While it is not apparent from FIG. 1 it will be understood by those skilled in the art that both the illumination system and the microscope 12 of the slit lamp microscope system pivot about a common vertical axis; that axis which passes through the viewing plane of the microscope. The viewing axes of the microscope may therefore straddle the 45 degree mirror 13, or the illumination system may be swung to one side or the other of the entire microscope, providing oblique illumination of the eye under examination.

With the apparatus of FIG. 1, having a target transparency fixed in position, the image of the target transparency is perfectly in focus only for one refractive condition of the patient's eye. If the target transparency is placed at the anterior focal plane of the converging lens, its image is in focus only for an eye having no refractive error. Even though the depth of focus of the patient's eye is substantially increased by the effective aerial pinhole aperture of the instrument, optimal operation requires that refractive errors be at least grossly corrected. Thus, with the target transparency in a fixed position, the patient must wear either glasses or a contact lens to correct any existing refractive errors. While this is usually not a problem, there are occasions where the proper spectacle or contact lens correction is not known, and it is useful to have the added capability within the instrument of varying the effective correction during measurement.

Figure 3:
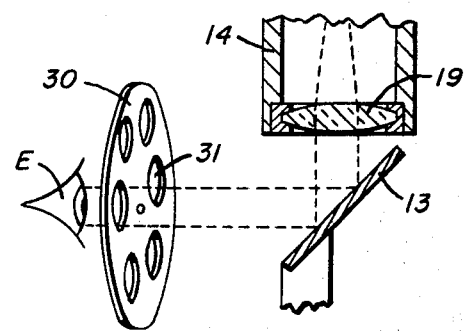
FIG. 3 is a partial view of the apparatus of FIG. 1 with the addition of a wheel of selectable trial lenses positioned before the patient's eye.

One method of varying the refractive correction during measurement is to provide a wheel of selectable trial lenses positioned before the patient's eye in the usual spectacle plane, as illustrated at 30 in FIG. 3. The trial lenses 31 in the wheel are spherical lenses, both diverging and converging, of graduated powers, to correct various amounts of refractive error, both myopia (diverging lenses) and hyperopia (converging lenses). With these selectable trial lenses located in the ordinary spectacle plane, magnification of the image of the target transparency as viewed by the patient would be identical to the magnification produced by ordinary spectacle correction of the patient's refractive error.

Another method of correcting the patient's refractive error during measurement of potential visual acuity is shown in the modified form of the invention in FIG. 4. Here the target transparency is made movable along the axis of the illumination system. It is mounted in a movable barrel 32 having a rack formation 33 on one outer side-wall thereof adapted to be driven by a pinion 34 connected to a knurled thumb wheel 35. This provides a limited range of refractive correction. There is a major disadvantage of the apparatus of FIG. 4, however, for the magnification of the visual acuity figures changes with different amounts of refractive correction dialed in.

This disadvantage may be overcome by an adaptation of the apparatus of FIG. 4, as shown in FIG. 5. The converging lens 19 has been changed to such a power that its posterior focal plane is proximate to the patient's eye, ideally coinciding with the spectacle plane of the patient. For the illuminated aperture 15 to still be imaged at the patient's eye, an additional converging lens 36 had to be added in fixed position above the target transparency 20, but this presents no problem.

With the arrangement of FIG. 5, the movable target transparency and the converging lens having its posterior focal plane in the vicinity of the eye constitute an optometer system. As the target transparency 20 is moved axially, the amount of refractive correction provided at the posterior focal plane of the converging lens 19 varies linearly with displacement of the target transparency. If the target transparency is at the anterior focal plane of the converging lens, the refractive correction at the posterior focal plane of the converging lens is zero. If the target transparency 20 is moved toward the lens 19, the refractive correction produced in the posterior focal plane of the converging lens becomes minus, changing linearly in diopters with movement of the target transparency. Likewise, movement of the target transparency away from the converging lens changes the refractive correction in the posterior focal plane of the converging lens in the plus direction, changing linearly in diopters with axial movement of the target transparency. This is the well-known optometer principle.

The magnification of the image of the target transparency, relative to the position of the posterior focal plane of the converging lens, remains constant in this arrangement. This particular optometer arrangement, with the posterior focal plane of the converging lens in the spectacle plane, simulates variable spherical correction in the spectacle plane, with magnification identical to that which would be obtained with a variable-power spectacle lens in this location. If the posterior focal plane of the converging lens were made to fall in the position of the patient's pupil, magnification of the image of the target transparency would be constant regardless of the refractive correction provided by axial movement of the target transparency. This latter arrangement is the familiar Badal type of optometer. Whether the optometer system produces no magnification, change with various refractive corrections, or whether magnification is identical to that produced by spectacle lenses is simply a matter of preference, and is dependent upon the chosen location of the posterior focal plane of the converging lens.

The range of refractive correction available in apparatus such as that of FIG. 5 is fairly limited. This range may be increased by replacement of the single converging lens 19 with a converging lens system having an equivalent focal length which is substantially shorter than the focal length of the single converging lens of FIG. 5. Such a converging lens system is shown in FIG. 6, with the converging lens system comprising two converging lenses 40 and 41 of +76.9 D and +39.0 D respectively, spaced 48 mm apart. Axial movement of the target transparency 20 in the arrangement of FIG. 6 provides from approximately +20.5 D to −24.0 D of refractive correction. Such a wide range of refractive correction is not possible if only a single converging lens is used. Two additional lenses 42 and 43 have been added in fixed position, to the arrangement of FIG. 6, a +57.8 D lens 42 located 20 mm from the illuminated aperture, and a −40 D lens 102.6 mm from the lens 42. These lenses collimate the light from the illuminated aperture 15 as well as compensate for the magnification change introduced by the converging lens system added below. These collimating and compensating lenses lengthen the slit lamp illumination column, but lenses such as these are necessary if the illuminated aperture is to be imaged in the correct position at the patient's eye, and with magnification consistent with proper operation of the examination function of the slit lamp microscope. Detailed specification of these lenses, however, is not germane to the principle of the present invention. Suffice it to say that appropriate lenses will be chosen in conjunction with the illuminated aperture such that the converging lens system beneath the target transparency will form an appropriate image of the illuminated aperture at the patient's eye.

It may be advantageous to provide a wide range of refractive correction without having to move the target transparency. For instance, if a wheel of selectable target transparencies is used, axial movement of the target transparency may be cumbersome. For this reason, the embodiment of the invention shown in FIG. 7 is proposed. The target transparency 20 in FIG. 7 is stationary, with collimated light from the illuminated aperture 15 passing through it toward the eye E. Between the target transparency and the converging lens, however, an astronomical telescope 50 has been added, comprising lenses 51 and 52 of +76.8 D and +28.6 D respectively, separated by a distance of 48 mm. Because the light from the illuminated aperture is collimated within the space occupied by the astronomical telescope, this light remains collimated regardless of the position of the telescope, and an image of the illuminated aperture is formed in the posterior focal plane of the converging lens, at the eye. The target transparency, however, is reimaged by the astronomical telescope into various positions, with the image of the target transparency moving axially in a linear relationship to movement of the astronomical telescope. Thus the combination of the target transparency and the movable astronomical telescope represents the optical equivalent of the movable target transparency of FIG. 5, but an optical equivalent providing a much larger range of refractive correction. From the furthest raised position to the furthest lowered position, the arrangement of FIG. 7 provides from −18 D to +20.5 D of refractive correction respectively. This refractive correction, with respect to the posterior focal plane of the converging lens, varies linearly with axial movement of the astronomical telescope. Also, magnification of the image of the target transparency remains constant with respect to the location of the posterior focal plane of the converging lens.

The arrangement of FIG. 7 is the only embodiment of the present invention which requires that the light from the illuminated aperture 15 be collimated in the space between the target transparency and the converging lens. If the light from the aperture were not collimated in this space, the location of the image of the illuminated aperture would change as the astronomical telescope is moved up and down. The same lenses 42 and 43 have been added above the target transparency in FIG. 7 as were added in FIG. 6 for collimation of the light from the illuminated aperture, nd also for compensation of magnification change produced by the added lenses beneath the target transparency. Again, details of these collimating and magnification compensation lenses are not germane to the principle of the present invention. Suffice it to say that an illuminated aperture and appropriate lenses are chosen which, in combination with the astronomical telescope and the converging lens, produce an image of the illuminated aperture of appropriate size at the patient's eye.

I claim:

1. In combination with a slit lamp having an illumination system and a microscope for examining the eye of a patient, the illumination system including a light source, aperture illuminated by said light source, and converging lens means interposed between said aperture and the eye to be examined, with said converging lens means forming an image of said aperture in the vicinity of the eye, the improvement comprising, said aperture being of pinhole size and a target transparency having figures of calibrated size thereon interposed in the slit lamp between said aperture and said converging lens means, whereby the target transparency figures are imaged by said converging lens means in order to determine the eyes' visual acuity.

2. Apparatus as defined in claim 1, wherein said converging lens means comprises a single converging lens.

3. Apparatus as defined in claim 1, wherein said converging lens means comprises at least two spaced apart converging lenses.

4. Apparatus as defined in claim 1 wherein said target transparency is positioned in the slit lamp substantially in the anterior focal plane of the converging lens means whereby a distant image of the figures on the transparency is presented to the eye.

5. Apparatus as defined in claim 1 and further including a plurality of trial lenses adapted for selective positioning adjacent to the eye under examination to neutralize the refractive error of said eye.

6. Apparatus as defined in claim 1 wherein said target transparency is secured to a mount movable along the axis of the illumination system, and means for moving said mount to properly adjust said target transparency axially whereby refractive error of the eye may be neutralized.

7. Apparatus as defined in claim 6, wherein the posterior focal plane of said converging lens means is proximate to the eye of the patient, whereby the degree of refractive error neutralized relative to said proximate position is directly proportional to the axial displacement of the target transparency from the anterior focal plane of said converging lens means.

8. Apparatus as defined in claim 7, wherein when the target transparency is located at the anterior focal plane of the converging lens means, the refractive correction at the posterior focal plane is zero, movement of the target transparency toward the converging lens means provides a minus refractive correction, and movement of the target transparency away from the converging lens means provides a positive refractive correction.

9. Apparatus as defined in claim 1 and further including a collimating lens means interposed between said aperture and said converging lens means to collimate the light from said aperture.

10. Apparatus as defined in claim 9, and further including a telescopic optical system located between said target transparency and said converging lens means, and means to cause movement of said telescopic optical system among the optical axis of said illumination system, whereby refractive error of the eye may be neutralized by optimal axial adjustment thereof.

11. Apparatus as defined in claim 10, wherein the posterior focal plane of said converging lens means is located proximate to the patient's eye, whereby the degree of refractive error neutralized relative to said proximate position is directly proportional to the axial displacement of the telescopic optical system.

* * * * *